US006846321B2

(12) United States Patent
Zucker

(10) Patent No.: US 6,846,321 B2
(45) Date of Patent: Jan. 25, 2005

(54) MECHANICAL METHOD AND APPARATUS FOR ENHANCING HEMOSTATIS FOLLOWING ARTERIAL CATHETERIZATION

(75) Inventor: Menachem Zucker, Kiryat Mutzkin (IL)

(73) Assignee: Cardiodex, Ltd., Tirat Hacarmael (IL)

( * ) Notice: Subject to any disclaimer, the term of this patent is extended or adjusted under 35 U.S.C. 154(b) by 266 days.

(21) Appl. No.: 10/283,839

(22) Filed: Oct. 30, 2002

(65) Prior Publication Data

US 2003/0055397 A1 Mar. 20, 2003

Related U.S. Application Data

(62) Division of application No. 09/598,232, filed on Jun. 21, 2000, now abandoned.

(51) Int. Cl.⁷ ................................................. A61D 1/00
(52) U.S. Cl. ...................... 606/213; 604/192; 604/194; 604/108; 604/508; 604/509
(58) Field of Search .......................... 600/207; 604/192, 604/194, 213, 201, 202, 203, 96.01, 508, 509, 103.06, 103.08; 128/898

(56) References Cited

U.S. PATENT DOCUMENTS

| 4,744,364 A | 5/1988 | Kensey |
| 4,836,204 A | 6/1989 | Landymore et al. |
| 5,217,024 A | 6/1993 | Dorsey et al. |
| 5,370,660 A | 12/1994 | Weinstein et al. |
| 5,413,571 A | 5/1995 | Katsaros et al. |
| 5,419,195 A | 5/1995 | Quinn |
| 5,540,715 A | * 7/1996 | Katsaros et al. ............ 606/213 |
| 5,700,277 A | 12/1997 | Nash et al. |
| 5,725,551 A | 3/1998 | Myers et al. |
| 5,728,134 A | * 3/1998 | Barak .......................... 606/214 |
| 5,928,266 A | 7/1999 | Kontos |
| 6,048,358 A | * 4/2000 | Barak .......................... 606/213 |
| 6,743,195 B2 | * 6/2004 | Zucker ................... 604/101.01 |

OTHER PUBLICATIONS

Overview of CompressAR. 2002.
Angio–Seal™, 2002.
The Prostar®; Perclose, Inc. 2002.

* cited by examiner

Primary Examiner—Glenn K. Dawson
Assistant Examiner—Darwin P Erezo
(74) Attorney, Agent, or Firm—Welsh & Katz, Ltd.

(57) ABSTRACT

A method for hemostasis of an artery having a puncture after arterial catheterization, the catheterization using an introducer sheath, the method including the steps of inserting into an artery a catheter introducer having a forward end and a balloon adjacent the forward end prior to arterial catheterization, following arterial catheterization and removal of a catheter from the catheter introducer, retracting the catheter introducer such that the forward end thereof lies exterior of the artery adjacent a puncture in the wall of the artery, inflating the balloon, thereby causing inward collapse of the forward end of the catheter introducer, thereby defining an enhanced surface area surrounded by the balloon adjacent the puncture for hemostasis, and following hemostasis, deflating the balloon and removing the catheter introducer from the patient.

An introducer sheath suitable for use in the method is also described and claimed.

5 Claims, 4 Drawing Sheets

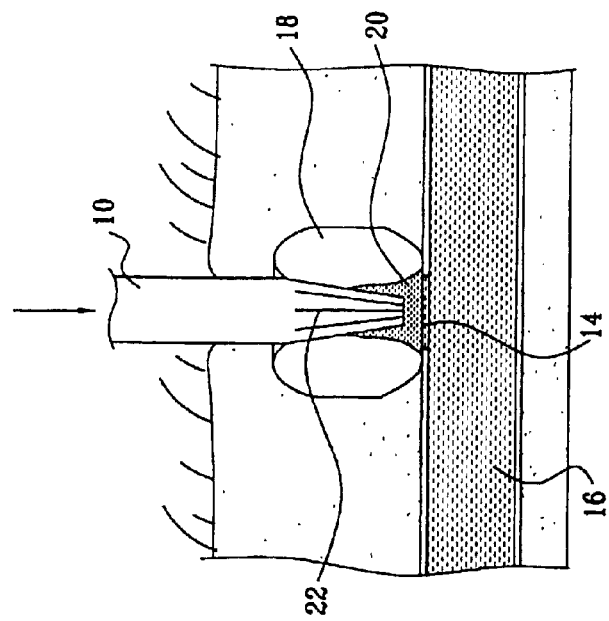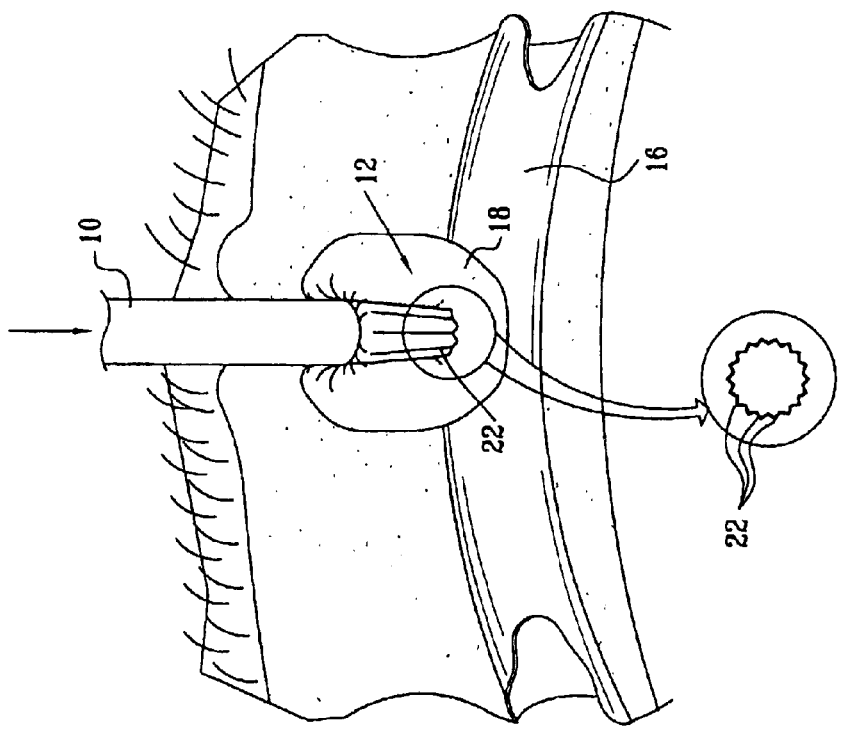

US 6,846,321 B2

MECHANICAL METHOD AND APPARATUS FOR ENHANCING HEMOSTATIS FOLLOWING ARTERIAL CATHETERIZATION

This appl is a Div of Ser. No. 09/598,232 Jun. 21, 2000 Abandoned.

FIELD OF THE INVENTION

The present invention relates to methods and apparatus for hemostasis following arterial catheterization.

BACKGROUND OF THE INVENTION

Various techniques are known for arterial catheterization. Following arterial catheterization, it is necessary to cause hemostasis quickly and without undue hardship for the patient.

Applicant's U.S. Pat. No. 6,048,358 and published PCT Applications WO 98/11830 and WO 00/02488 describe methods and apparatus for hemostatis which greatly simplify hemostasis and thus greatly reduce patient discomfort following arterial catheterization. These patent documents, the disclosures of which are hereby incorporated by reference and the prior art referenced therein are considered to represent the state of the art.

SUMMARY OF THE INVENTION

The present invention seeks to provide improved apparatus and techniques for hemostasis.

There is thus provided in accordance with a preferred embodiment of the present invention a method for hemostasis of an artery having a puncture after arterial catheterization, the catheterization using an introducer sheath, the method including the steps of:

inserting into an artery a catheter introducer having a forward end and a balloon adjacent the forward end prior to arterial catheterization;

following arterial catheterization and removal of a catheter from the catheter introducer, retracting the catheter introducer such that the forward end thereof lies exterior of the artery adjacent a puncture in the wall of the artery;

inflating the balloon, thereby causing inward collapse of the forward end of the catheter introducer, thereby defining an enhanced surface area surrounded by the balloon adjacent the puncture for hemostasis; and following hemostasis, deflating the balloon and removing the catheter introducer from the patient.

Preferably, the step of retracting the catheter introducer is effected by inflating the balloon to an extent less than that which causes the inward collapse of the forward end of the catheter introducer.

In accordance with a preferred embodiment of the present invention, the step of inflating the balloon causes the forward end of the catheter introducer to crease along multiple crease lines pre-formed therein.

Preferably, the inward collapse at least restricts the opening of the catheter introducer adjacent the puncture. Even more preferably, the inward collapse at least closes the opening of the catheter introducer adjacent the puncture.

There is also provided in accordance with a preferred embodiment of the present invention, for use in a method for hemostasis of an artery having a puncture after arterial catheterization, an introducer sheath having a crushable forward end, at least partially surrounded by a balloon and being operative such that inflation of the balloon causes inward collapse of the forward end of the catheter introducer, thereby defining an enhanced surface area surrounded by the balloon adjacent a puncture for hemostasis.

Preferably, the balloon is constructed and located such that initial inflation of the balloon is operative for retracting the catheter introducer from an artery.

In accordance with a preferred embodiment of the present invention, the crushable forward end includes multiple crease lines pre-formed therein.

BRIEF DESCRIPTION OF THE DRAWINGS

The present invention will be understood and appreciated more fully from the following detailed description taken in conjunction with the drawing in which:

FIGS. 1A, 1B, 1C and 1D are simplified pictorial illustrations of four stages in the operation of a catheter introducer assembly constructed and operative in accordance with a preferred embodiment of the present invention; and FIGS. 2A, 2B, 2C and 2D are simplified sectional illustrations of four stages in the operation of a catheter introducer assembly constructed and operative in accordance with a preferred embodiment of the present invention corresponding to the stages illustrated in FIGS. 1A–1D.

DETAILED DESCRIPTION OF A PREFERRED EMBODIMENT

Figure 2A:
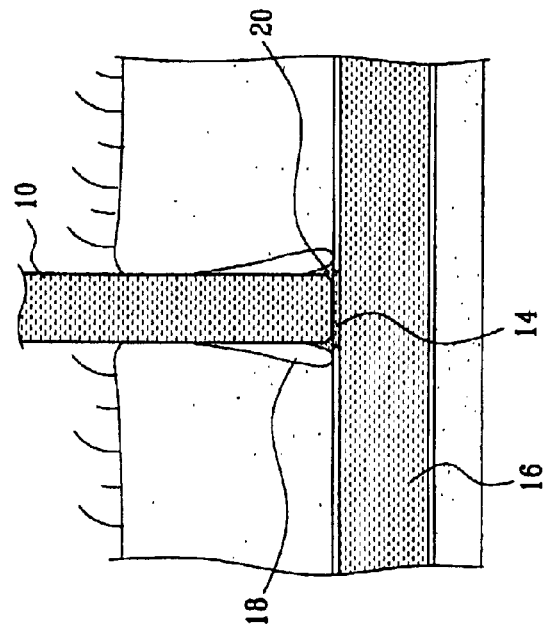
Figure 1A:
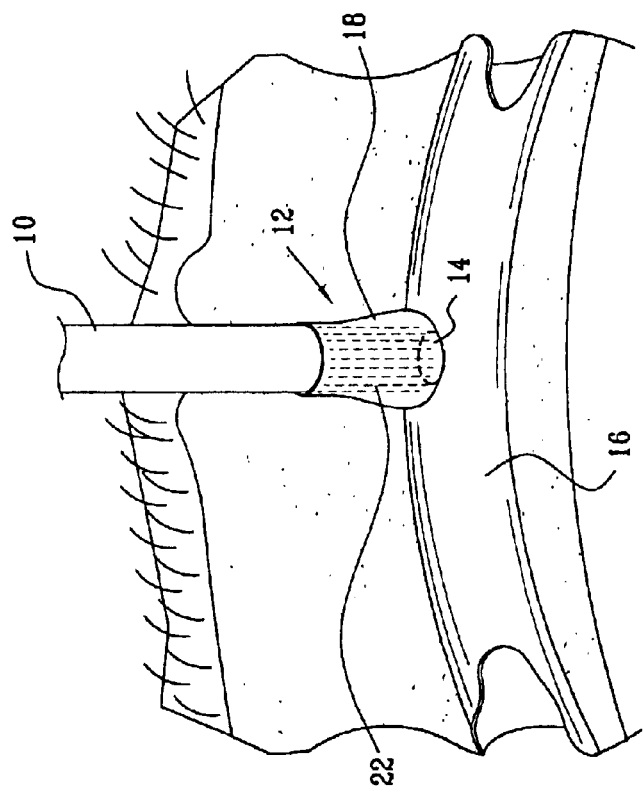

Reference is now made to FIGS. 1A and 2A, which illustrate a first stage in the operation of a catheter introducer assembly constructed and operative in accordance with a preferred embodiment of the present invention.

As seen in FIGS. 1A and 2A, a catheter introducer 10 is shown following catheterization and following withdrawal of a catheter therefrom, such that an extreme end 12 of the catheter introducer lies adjacent to and outside a puncture 14 in an artery 16. An external balloon 18 is disposed adjacent extreme end 12 and is shown in a partially-inflated orientation, to a first pressure, typically less than 1 atm. wherein the balloon 18 forms a skirt surrounding and sealing puncture 14 from the tissue external thereto. At this stage blood normally fills artery 16 as well as puncture 14 and catheter introducer 10, as well as the annular volume 20 surrounded by balloon 18 adjacent puncture 14 and extreme end 12.

It is a particular feature of the present invention that the catheter introducer 10 is formed to be crushable adjacent extreme end 12. The crushable structure may be realized in any suitable manner, such as by pre-forming crease lines 22 therein.

Figure 1B:
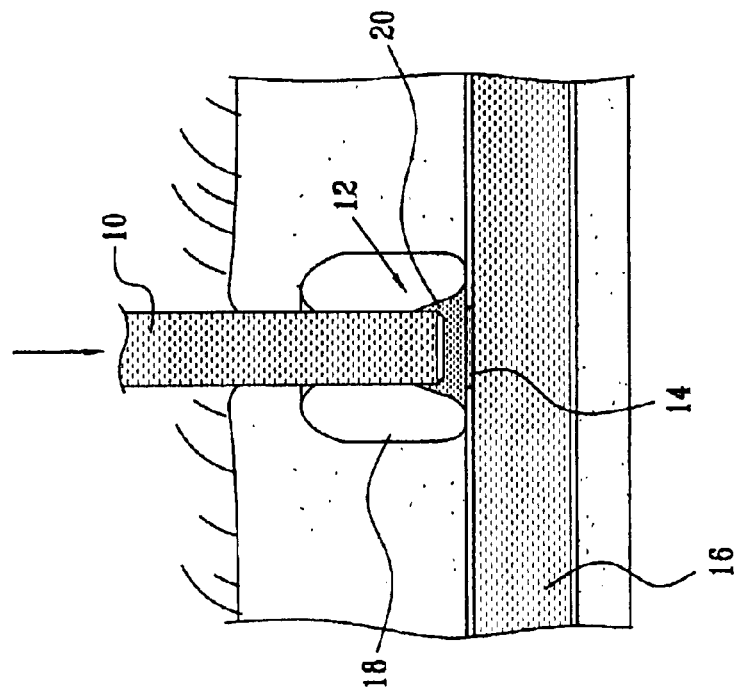
Figure 2B:
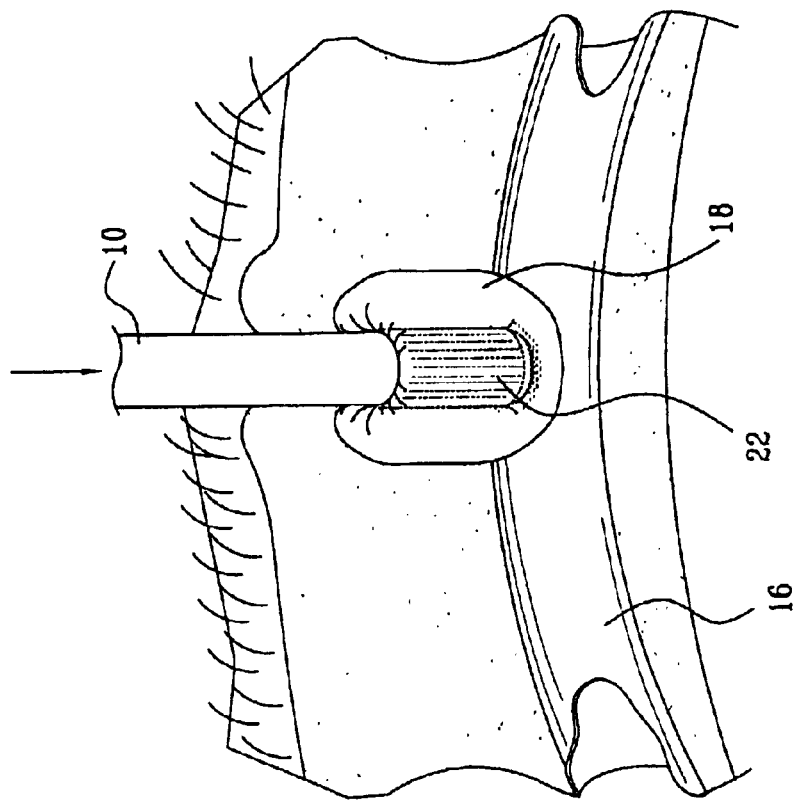

Reference is now made to FIGS. 1B and 2B, which illustrate a second stage in the operation of a catheter introducer assembly constructed and operative in accordance with a preferred embodiment of the present invention. Here balloon 18 is fully inflated to a second pressure, typically 1–1.5 atm., further displacing extreme end 12 from puncture 14 and enlarging volume 20 in which blood begins to coagulate.

Reference is now made to FIGS. 1C and 2C, which illustrate a third stage in the operation of a catheter introducer assembly constructed and operative in accordance with a preferred embodiment of the present invention. Here balloon 18 is fully inflated to a third pressure, typically 1.5–2 atm., at which pressure crushing of the end of the catheter introducer 10 adjacent extreme end 12 along crease lines 22 begins to take place, as shown.

Figure 2D:
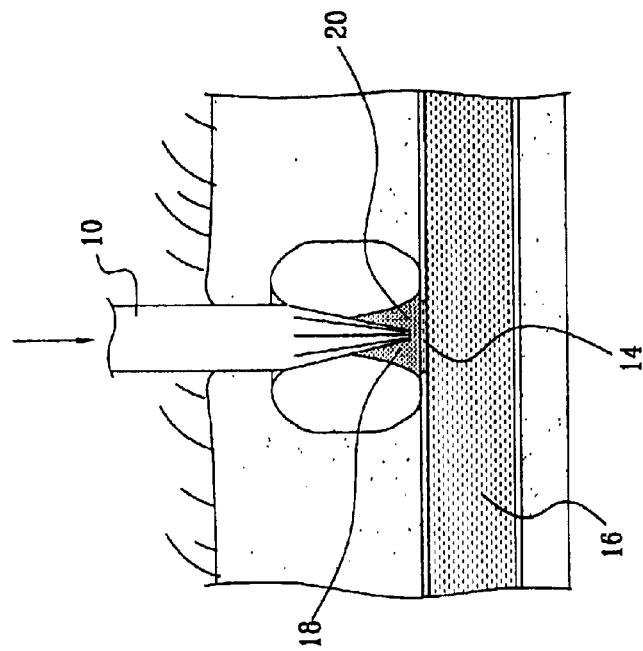
Figure 1D:
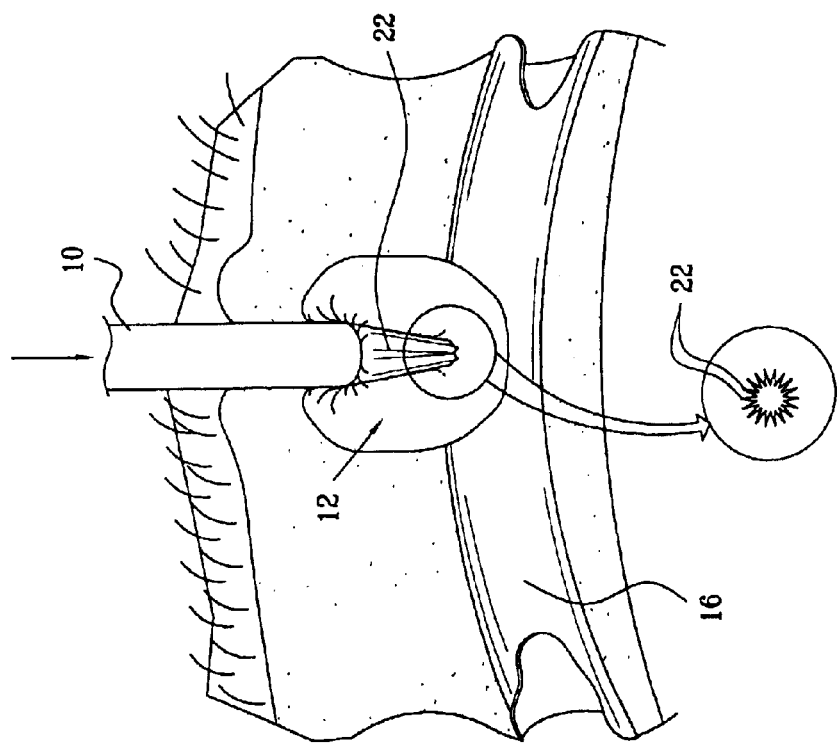

Reference is now made to FIGS. 1D and 2D, which illustrate a fourth stage in the operation of a catheter introducer assembly constructed and operative in accordance with a preferred embodiment of the present invention. Here balloon 18 is fully inflated to a fourth pressure, typically greater than 2 atm., at which pressure crushing of the end of the catheter introducer 10 adjacent extreme end 12 along crease lines 22 is completed, as shown.

It is appreciated that the functionality shown in FIGS. 1A–1D and 2A–2D is a generally continuous function, which is illustrated at various stages thereof. The crushing of the forward end of the catheter introducer 10 produces increased surface area at volume 20, which enhances the speed and completeness of hemostasis. This surface area lies both along interior facing surfaces of balloon 18 and along exterior facing surfaces of the crushed portion of the catheter introducer 10 adjacent extreme end 12. At the same time, crushing of the forward end of the catheter introducer 10 closes the opening therein and restricts and possible eliminates contact between the blood in volume 20 and the uncoagulated blood within the catheter introducer 10, thus also enhancing the speed and completeness of hemostasis.

Upon completion of hemostasis, the balloon 18 may be deflated and the catheter introducer 10 may be removed from the patient.

It will be appreciated by persons skilled in the art that the present invention is not limited by what has been particularly shown and described hereinabove. Rather the scope of the present invention includes both combinations and sub-combinations of the various features described hereinabove as well as variations and modifications which would occur to persons skilled in the art upon reading the specification and which are not in the prior art.

What is claimed is:

1. A method for hemostasis of an artery having a puncture after arterial catheterization, said catheterization using an introducer sheath, the method comprising the steps of:

inserting into an artery a catheter introducer having a forward end and a balloon adjacent said forward end prior to arterial catheterization;

following arterial catheterization and removal of a catheter from the catheter introducer, retracting the catheter introducer such that the forward end thereof lies exterior of the artery adjacent a puncture in the wall of the artery;

inflating said balloon, thereby causing inward collapse of said forward end of said catheter introducer, thereby defining an enhanced surface area surrounded by said balloon adjacent said puncture for hemostasis; and following hemostasis, deflating said balloon and removing said catheter introducer from the patient.

2. A method for hemostasis of an artery having a puncture after arterial catheterization according to claim 1 and wherein said step of retracting the catheter introducer is effected by inflating said balloon to an extent less than that which causes said inward collapse of said forward end of said catheter introducer.

3. A method according to claim 2 and wherein said step of inflating said balloon causes said forward end of said catheter introducer to crease along multiple crease lines pre-formed therein.

4. A method according to claim 1 and wherein said inward collapse at least restricts the opening of said catheter introducer adjacent said puncture.

5. A method according to claim 1 and wherein said inward collapse at least closes the opening of said catheter introducer adjacent said puncture.

* * * * *